United States Patent [19]

Schneider et al.

[11] Patent Number: 4,795,449

[45] Date of Patent: Jan. 3, 1989

[54] FEMALE URINARY INCONTINENCE DEVICE

[75] Inventors: Barry L. Schneider, Deerfield; Joseph S. Tokarz, Palatine, both of Ill.

[73] Assignee: Hollister Incorporated, Libertyville, Ill.

[21] Appl. No.: 892,795

[22] Filed: Aug. 4, 1986

[51] Int. Cl.$^4$ ................................................. A61F 5/44
[52] U.S. Cl. ..................................... 604/329; 604/129; 604/323; 604/324; 604/326
[58] Field of Search ............... 604/128, 129, 323–326, 604/335, 327–331, 347–351; 4/144.1–144.4; 128/760, 761, 766, 768

[56] References Cited

U.S. PATENT DOCUMENTS

| | | | |
|---|---|---|---|
| 2,483,079 | 9/1949 | Williams | 128/295 |
| 3,194,238 | 7/1965 | Breece, Jr. | 604/329 |
| 3,529,599 | 9/1970 | Folkman et al. | 604/350 |
| 3,683,914 | 8/1972 | Crowley | 128/285 |
| 3,776,235 | 12/1973 | Ratcliffe | 128/295 |
| 3,830,241 | 8/1974 | Dye et al. | 604/129 |
| 3,861,394 | 1/1975 | Villari | 604/129 |
| 4,160,383 | 7/1979 | Rauschenberger | 604/323 |
| 4,194,508 | 3/1980 | Anderson | 604/329 |
| 4,198,979 | 4/1980 | Cooney et al. | 604/329 |
| 4,270,539 | 6/1981 | Frosch | 128/295 |
| 4,328,828 | 5/1982 | Cranci | 128/768 |
| 4,421,511 | 12/1983 | Steer | 604/329 |
| 4,484,917 | 11/1984 | Blackmon | 604/329 |
| 4,496,355 | 1/1985 | Hall et al. | 604/329 |
| 4,563,183 | 1/1986 | Barrodale et al. | 604/329 |
| 4,583,983 | 4/1986 | Einhorn et al. | 604/329 |

FOREIGN PATENT DOCUMENTS

| | | | |
|---|---|---|---|
| 0018749 | 11/1980 | European Pat. Off. | 604/329 |
| 2015347A | 4/1979 | United Kingdom . | |
| 2070936A | 3/1980 | United Kingdom . | |
| 2126902 | 4/1984 | United Kingdom | 604/330 |

Primary Examiner—C. Fred Rosenbaum
Assistant Examiner—Mario Costantino
Attorney, Agent, or Firm—Tilton, Fallon, Lungmus

[57] ABSTRACT

A female urinary incontinence device including a periurethral cup having a neck portion with laterally outwardly facing adhesive surfaces for sealingly engaging the inwardly facing surfaces of the labia minora (also the labia majora) to provide an effectively sealed flow path for urinary outflow into a collection receptacle. In a preferred embodiment, a second adhesive zone is also provided along the rim of the cup for sealing engagement with the periurethral floor. A one-way valve and a vent are also included to prevent backflow, protect the adhesive seals, and provide vacuum relief even at low urinary flow rates.

26 Claims, 3 Drawing Sheets

U.S. Patent  Jan. 3, 1989  Sheet 1 of 3  4,795,449
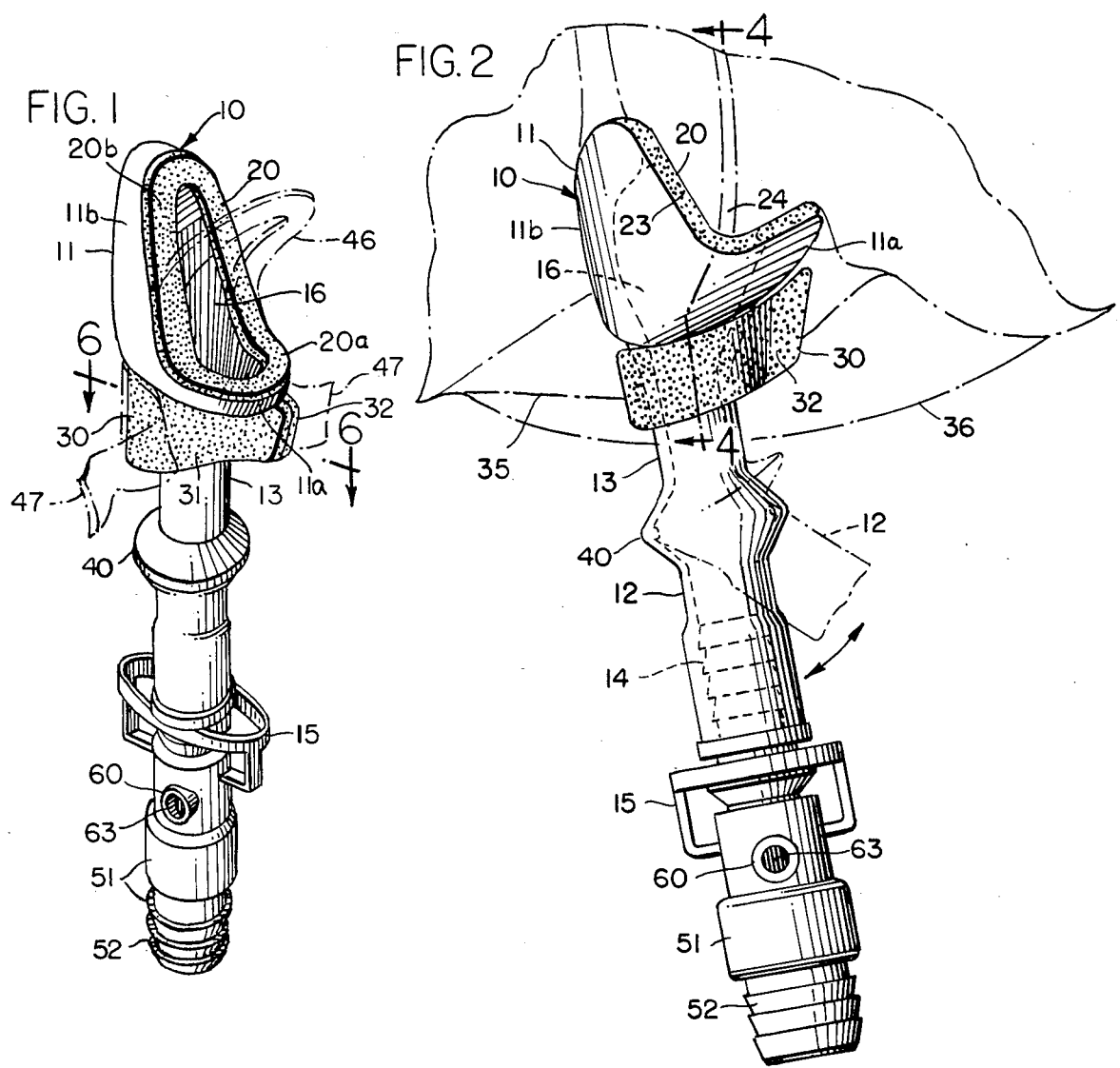
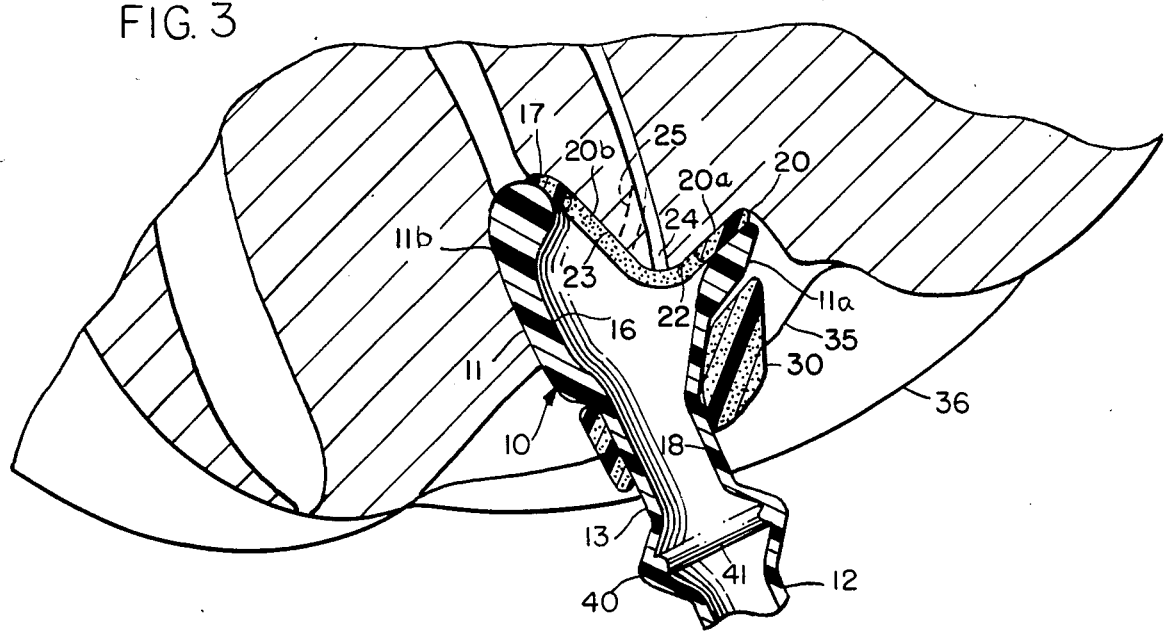

FEMALE URINARY INCONTINENCE DEVICE

BACKGROUND AND SUMMARY

Various devices have been proposed in past years for directing and collecting urine from female patients suffering from urinary incontinence but, in general, such devices have been associated with problems of leakage, wearer discomfort, pressure sores, and even necrosis Lack of commercialization is evidence of the ineffectiveness of earlier devices.

Prior patents have disclosed female urinary collection devices equipped with locating elements intended to be inserted into the vagina for retaining the collection devices in operative positions. Reference may be had, for example, to U.S. Pat. Nos. 2,483,079, 3,776,235 and 4,198,979. Constructions with relatively rigid locating elements clearly fail to conform with the anatomical changes occurring during body movement; other devices with flexible or deformable vaginal locating elements may reduce tissue irritation and increase patient comfort, but problems in providing an effective seal and avoiding leakage along the lines or zones of contact nevertheless remain.

U.S. Pat. No. 4,198,979 discloses a rigid-type collection device with a pommel for vaginal insertion. The orifice of the rigid collector is covered with a sealant layer of body adhesive for contact with vestibular tissue. U.S. Pat. No. 3,683,914 presents a device with an enlarged vaginally-insertable portion with a separate passage leading to a collection tube. U.S. Pat. Nos. 4,421,511 and 3,194,238 both disclose female incontinence devices with inner cups or funnels intended to engage the periurethral floor and external pads engagable with a wearer's skin about the labia majora. A suitable harness or belt is then worn to help hold the external and internal elements in place.

Published British application No. 2,090,741A discloses an incontinence device having an adhesive pad of triangular shape intended to engage periurethral tissue. British application No. 2,015,374A shows an incontinence device including an adhesive pad with a ridge-like projection dimensioned to extend between the labia majora of a wearer. U.S. Pat. No. 4,563,183 shows a female external catheter with an intralabial adhesive body for engaging the vestibule and an interlabial adhesive body that overlies and adhesively contacts the external aspects of the labia minora.

Co-pending co-owned U.S. Pat. No. 4,681,572, discloses a female urinary incontinence device having a periurethral cup, an external pad, and an elastic tubular bellows extending between the cup and pad. The periurethral cup is molded in one piece from soft compressible material having a durometer within the range of about 10 to 30 on the Shore A scale and has walls of substantial thickness providing smoothly rounded surfaces for sealingly contacting surfaces of the periurethral floor and vaginal introitus. One wall portion of the cup curves upwardly to define a resilient urine-reflecting protuberance received within the vaginal introitus. The external pad is held in place by a panty or belt to keep the bellows in a state of partial compression, the compressed bellows in turn holding the periurethral cup in proper position.

Other patents of interest are U.S. Pat. Nos. 4,270,539, 4,496,355, and published British application No. 2,070,936A.

The incontinence device of this invention includes a periurethral cup that is formed from highly resilient and deformable material and has a configuration similar to the cup disclosed in the aforementioned co-pending patent. However, there is no resilient bellows, nor must there be any external pad or other direct external retention means. Two zones of adhesive contact effectively maintain the cup in place.

Specifically, a first resilient adhesive pad extends about the neck portion of the periurethral cup and has a pair of side sections with enlarged laterally and outwardly facing surfaces for adhesively engaging the inwardly-facing surfaces of the labia minora of the patient. While the first adhesive pad may also contact the inwardly-facing or opposing surfaces of the labia majora, such pad is in any event enclosed between the labia minora when the device is properly worn. The pad may take the form of a band of adhesive material wrapped about the neck portion of the periurethral cup with the ends of the band joined together to form a double-thickness flap projecting forwardly from the cup's neck portion.

The second resilient adhesive pad is of annular shape and is affixed to the rim of the periurethral cup for adhesively and sealingly engaging the periurethral floor. It has been found that the first sealing zone performs a retentive function that cannot be accomplished by the second zone alone, and that the two zones coact to maintain the cup in effective sealing contact with a wearer.

The device also includes a detachable coupling in close proximity to the periurethral cup. Adjacent the point of detachable interconnection are a one-way membrane flap valve, which prevents backflow that might otherwise disrupt the adhesive seals, and a disc-equipped vent valve which blocks the escape of urine but allows entry of ambient air to provide vacuum relief even at extremely low rates of urinary flow. Other features, advantages, and objects of the invention will become apparent from the specification and drawings.

DRAWINGS

FIG. 1 is a perspective view of a female urinary incontinence device embodying the present invention.

FIG. 2 is a side elevational view of the cup shown as it would be worn by a patient.

FIG. 3 is a view similar to FIG. 2 but showing the cup in longitudinal section.

DETAILED DESCRIPTION OF PREFERRED EMBODIMENT

Figure 4:
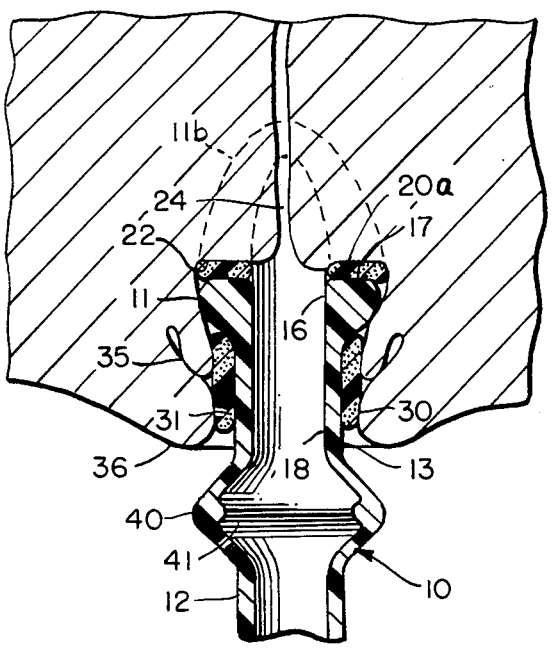
FIG. 4 is a longitudinal sectional view taken along line 4—4 of FIG. 2.
Figure 5:
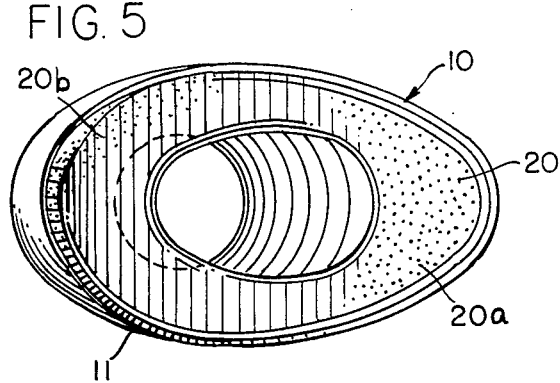
FIG. 5 is an enlarged top plan view of the cup.

Referring to the drawings, the numeral 10 generally designates a female urinary incontinence device including a periurethral cup 11 and a flexible outlet tube 12 that is formed integrally with the neck portion 13 of the cup. A tubular connector 14 of polypropylene or other relatively rigid polymeric material is tightly and sealingly received within the lower end of the outlet tube 12 and is detachably connected to a coupling member 15 which in turn is adapted for connection to a suitable drainage tube (not shown). The mechanical coupling between connector 14 and member 15 is similar to that shown and described in U.S. Pat. No. 4,280,498. While that coupling assembly is believed particularly effective, other types of detachable couplings may instead be used.

The periurethral cup 11, neck portion 13, and outlet tube 12 are molded in one piece from a soft, resilient, elastomeric material such as silicone rubber. A silicone elastomer such as manufactured by Dow Corning under the designation Q7-4840 is suitable, but other elastomers of silicone rubber, polyurethane, latex, or any of a variety of other materials having similar properties, may be used. Regardless of the material selected, it is believed important that such material should have a durometer within the range of about 10 to 30 on the Shore A scale, preferably with the range of 20 to 25.

It will be observed that the cup 11 has front and rear portions 11a and 11b, respectively, the rear portion projecting upwardly to provide a vaginally-insertable urine-deflecting protuberance. The front and rear portions together define an upwardly-opening urine-receiving cavity 16 having a continuous rim 17 that faces generally upwardly along the front portion 11a of the cup and both upwardly and forwardly along the rear protuberant portion 11b of the cup. The cavity communicates directly with the downwardly-extending passage 18 of the neck portion 13 as shown in FIGS. 3 and 4.

Secondary adhesive means in the form of a resilient annular adhesive pad 20 is affixed to the rim 17 along its full extent. The pad 20 has a front section 20a extending along the rim of the cup's front portion 11a and a rear section 20b extending along the rim of the cup's rear protuberant portion 11b. When the cup is properly positioned, the front section of the resilient adhesive pad 20 sealingly engages the periurethral floor 22 of the patient and the rear section sealingly engages the anterior surface of the vaginal introitus 23 (FIG. 3).

The main purpose of the protuberant rear portion 11b of the cup is to serve as a urine deflector for that proportion of the female population, estimated at between 15 to 20%, whose urethral orifice 24 is located within, or immediately adjacent to, the vaginal introitus. Such a location is indicated by broken lines 25 in FIG. 3. Any function the protuberance performs in retaining the cup in position is of secondary significance since, as described more fully hereinafter, retention is achieved mainly by the primary adhesive sealing zone, or by the coaction of the primary and secondary adhesive sealing zones, provided by the cup.

Figure 6:
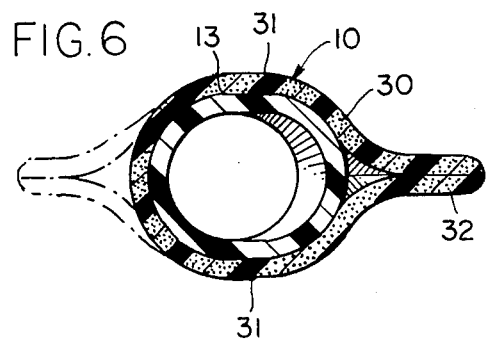
FIG. 6 is an enlarged cross sectional view taken along line 6—6 of FIG. 1.
Figure 7:
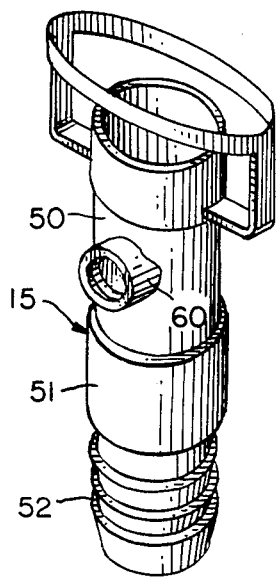
FIG. 7 is a perspective view of the coupling assembly that constitutes part of this invention.

The primary adhesive means takes the form of a resilient adhesive pad 30 that is externally affixed to the neck portion 13 directly beneath the cup 11. As shown clearly in FIG. 4, the width of neck portion 13 is substantially less than that of cup 11. Adhesive pad 30 includes a pair of side sections 31 extending along opposite sides of the neck portion 13 for adhesively engaging the inwardly-facing side surfaces of the labia minora 35, and preferably also the labia majora 36, of the wearer. The two side sections of the adhesive pad may be formed of two pieces or strips secured to opposite sides of the neck portion with their ends projecting forwardly and rearwardly beyond the neck portion as indicated partly in phantom in FIG. 6; however, in the preferred embodiment, the adhesive pad is formed from a single strip or band of material that is wrapped about the rear side of the neck portion with the ends of the band joined together to form a double-thickness flap 32 projecting forwardly from the neck directly beneath the front portion of the cup FIGS. 3 and 4 also reveal that the pad or strip 30 is relatively thin; that is, the pad has a vertical dimension that is substantially greater than its thickness.

The laterally-facing retention pad 30, as well as the annular sealant pad 20, may be formed of any suitable adhesive material of a type well known in the art. Such an adhesive is commonly made from the mixture of gelatin, pectin, sodium carboxymethylcellulose and polycarbons such as polyisobutylene. The adhesive sealant material has the general consistency of putty and is deformable in use to conform with the contour of the tissues against which it is sealed. A particularly effective sealant pad material useful for purposes of this invention is sold under the trademark "Hollihesive" by Hollister Incorporated, Libertyville, Illinois, but other resilient, deformable body adhesives are commercially available and may be used.

While the second sealing pad 20 performs a retentive function, its main function is to maintain an effective seal about the urethral orifice. For that purpose, it is important that the pad 20, and the rim on which it is mounted, curve smoothly and gradually in the area of transition between the front and rear portions 11a and 11b of the cup. An effective seal may be maintained even when the patient moves about because of the resilience and deformability of the cup and its integral neck portion Retention of the cup in its sealing contact with the urethral meatus results largely from the first sealant pad 30 which is carried by the neck portion and engages the inner or opposing surfaces of the labia 35 and 36. In that connection, it is to be noted that the forwardly-extending flap 32 of the pad 30 extends along the midline between the labia and that pad 30 provides enlarged lateral contact surfaces for engagement by and retention between the labia. For such purposes, the pad 30 should have a vertical dimension (i.e., a dimension extending along neck 13) within the range of about 5 to 20 millimeters, and the total width of the neck 13 and pad 30 should not exceed 18 (preferably 10 to 16) millimeters. Such relationships insure that when the urinary incontinence device is properly fitted, the labia minora, and preferably also the labia majora, will close against opposite sides of the adhesive pad 20 of the neck portion 13 to maintain the device in operative position.

Directly below the neck portion 13 is an integral enlargement 40 of slightly lesser wall thickness than that of the neck portion and outlet tube portion directly above and below the enlargement. A thickened section 41 within the enlargement maintains the passage in open condition even when the outlet tube is sharply bent as shown, for example, in broken lines in FIG. 2.

The urinary incontinence device is supplied for use by the patient with the exposed surfaces of the resilient adhesive pads 20 and 30 covered by release sheets 46 and 47 depicted in phantom in FIG. 1. In that figure, the release sheets, which may be formed of silicone-coated paper or any other suitable material, are shown partially peeled away from the resilient adhesive pads. In preparation for application, the user first removes the release sheet 46 from the periurethral cup, urges the labia apart, and positions the adhesive pad 20 against the urethral meatus with the protuberant urine-deflecting portion of the cup protruding slightly into the vagina. The cup is held gently in place until portion 20b of the adhesive pad seals against the anterior surface of the vaginal introitus and portion 20a seals against the periurethral floor. Release film 47 is then removed from the neck pad 30 and the labia minora, and also preferably the labia majora, are allowed to close against the resilient adhesive barrier material beneath cup 11. Coupling member 15, which is joined to a drainage tube and collection bag (not shown), is then coupled to tubular connector 14.

FIGS. 7-12 illustrate features of the coupling member 15 with particular emphasis on the valving and venting means provided thereby. Member 15 includes a tubular body 50 composed of upper and lower coaxial sections 51 and 52, respectively. The sections are telescoped together and permanently interconnected by turning lip 53 of the upper (outer) section inwardly about the shoulder 54 of the lower (inner) section 52. The rim of a one-way flap valve 55 is tightly clamped between annular end faces 51a and 52a of the respective sections as shown most clearly in FIG. 12.

Figure 11:
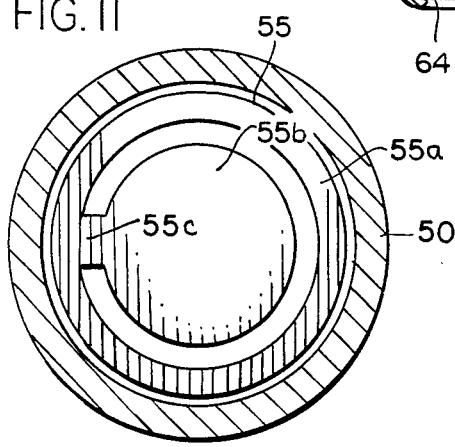
FIG. 11 is an enlarged sectional view taken along line 11—11 of FIG. 9.

Flap valve 55 is formed of elastomeric material and takes the form of a membrane having an outer annular rim portion 55a and an inner concentric flap portion 55b, the two portions being connected by an integral web or hinge 55c (FIG. 11). The upper section 51 of the tubular body 50 is provided with an annular valve seat 57 that is engaged by the flap portion 55b when the valve is in its normally closed position. However, the valve opens easily at extremely low urine flow rates; the weight of a small amount of urine on the upstream side of flap portion 55, or the low pressure conditions created when the flow is no more than a trickle (even when the axis of body 50 is horizontal) will cause the valve to open. However, should conditions develop that might lead to a reverse direction of flow, the flap valve tightly closes to block such reverse flow and protect the areas of sealing contact between skin barrier pads 20, 30 and the skin surfaces of the patient against sudden high back pressures that might disrupt the integrity of such seals.

Figure 12:
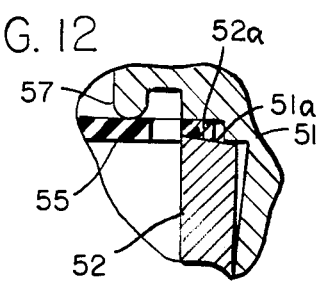
FIG. 12 is a greatly enlarged fragmentary view illustrating details of the one-way flap valve.

While the membrane flap valve 55 may be formed of any suitable elastomeric material, effective results have been obtained with a valve formed of silicone rubber having a durometer of 80 on the Shore A scale and a thickness of about 0.02 inches. It will be observed that in addition to providing retention means for the flap valve 55, the outer annular portion 55a of that valve also serves as a resilient sealing gasket between end faces 51a and 52a of sections 51 and 52 (FIG. 12).

Figure 8:
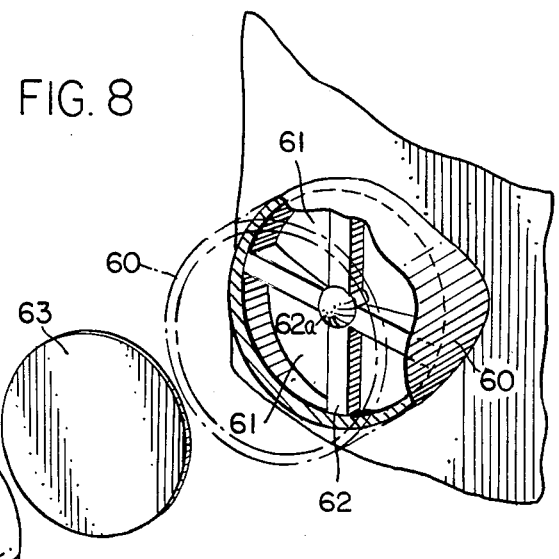
FIG. 8 is an enlarged fragmentary and exploded perspective view of the venting valve.
Figure 10:
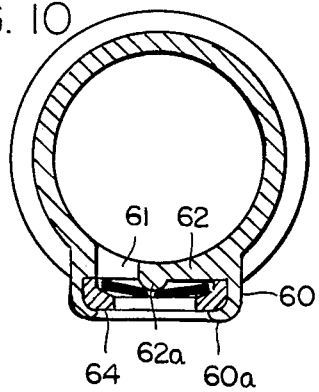
FIG. 10 is an enlarged sectional view taken along line 10—10 of FIG. 9.
Figure 9:
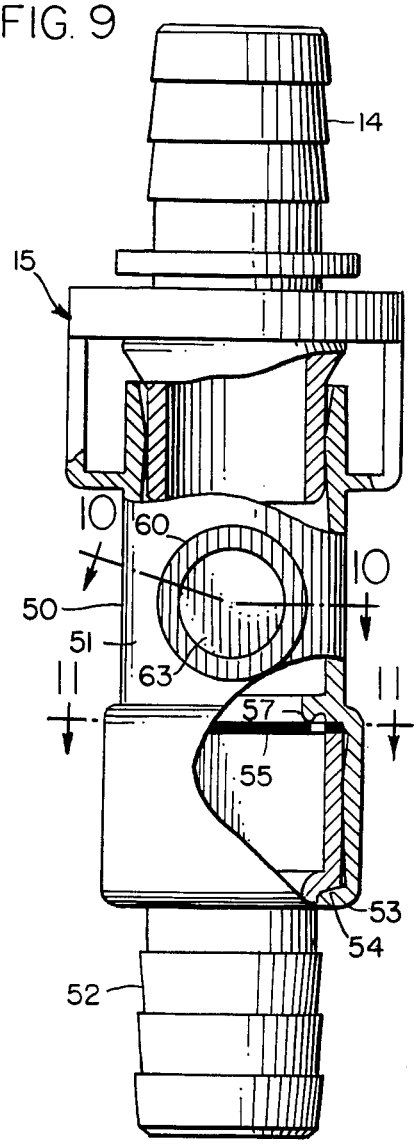
FIG. 9 is an elevational view, partly in section, of the coupling.

Upstream of flap valve 55 is a second one-way valve 60 that functions as an air vent. As shown in FIGS. 7-10, the upper section 51 of the tubular body has a lateral extension 60 that defines an inlet passage 61. A grid 62, formed integrally with the tubular 50 and its extension 60, is disposed within passage 61 (FIG. 8). The grid includes a projection 62a which is centrally located in passage 61 and protrudes outwardly, that is, away from the axis of body 50. A thin elastomeric disc 63 has its central portion engaged by projection 62a and has its periphery normally in contact with an annular valve seat member 64, the latter in turn being retained by an inwardly turned bead or rim 60a of lateral extension 60 (FIG. 10).

The valve seat 64 and projection 62a are positioned so that normally the valve is closed with disc 63 deformed slightly into a concave configuration and with its periphery tightly and sealingly engaging peripheral seat member 64. An increase in pressure within the tubular body section 51 only causes the disc to seat more tightly. Therefore, leakage is prevented by the disc and its seat as urine flows through the lumen of the tubular section 51. However, should even a slight vacuum tend to develop within the system, as where urination has stopped (or is diminished) but a column of liquid remains in the drainage tube of the system downstream of coupling member 15, disc 63 will readily flex along its periphery to crack open the vent valve and assure vacuum relief even at extremely low flow rates. For example, utilizing an imperforate disc formed of silicone rubber (having a durometer of 25 on the Shore A scale) of approximately 0.015 inches in thickness, such a vent valve has been found to have a cracking pressure of only 0.045 psi. It is to be understood, however, that other durometers, thicknesses, and elastomeric materials (such as latex) may be used to achieve similar results.

The vent valve is particularly important because it prevents the development of negative pressures in the system that might otherwise collapse the resilient tubing of the system (obstructing further flow of liquid), or distort the tissues in contact with the sealant pads of the device, or disrupt the seals between such pads and the body tissues.

While in the foregoing we have disclosed an embodiment of the invention in considerable detail for purposes of illustration, it will be understood by those skilled in the art that many of these details may be varied without departing from the spirit and scope of the invention.

We claim:

1. A female urinary incontinence device comprising a periurethral cup formed of soft elastomeric material having an upwardly-opening urine-receiving cavity and having a continuous rim extending about the opening of such cavity; said cup also including front and rear portions and an integral downwardly-extending neck portion of reduced width having a passage communicating with said cavity, said neck portion being provided with connecting means for connection to a drainage tube; and resilient adhesive pad means externally affixed to said neck portion; said pad means comprising at least one strip of pressure-sensitive adhesive material including a pair of side sections providing enlarged laterally-facing adhesive surfaces extending longitudinally along opposite sides of said neck portion for adhesively engaging the inwardly-facing side surfaces of the labia minora of a patient.

2. The device of claim 1 in which said side sections of said pad means extend forwardly beyond said neck portion.

3. The device of claims 1 or 2 in which said pad means has a dimension measured longitudinally of said neck portion within the range of about 5 to 20 millimeters.

4. The device of claim 3 in which said neck portion with said adhesive pad means thereon have a maximum outside lateral dimension within the range of 10 to 16 millimeters.

5. The device of claims 1 or 2 in which said pad means comprises a single strip of adhesive material wrapped about the rear side of said neck portion with the end portions of said strip joined together to form a double-thickness flap projecting forwardly from said neck portion directly beneath said cup.

6. The device of claim 1 in which said neck portion is connected to and communicates with a tubular member having one-way valve means therein for preventing a reverse flow of urine into said neck portion and said cup; and vent means between said valve means and said neck portion for permitting the entry of ambient air into said neck portion when ambient pressure exceeds the pressure within said tubular member.

7. The device of claim 6 in which said vent means comprises a lateral passage in said tubular member having a valve seat therein; a resilient, imperforate valve disc disposed within said passage having its periphery normally engaging said seat to prevent the escape of urine from said tubular member but being capable of flexing away from said seat to permit the entry of air when ambient pressure exceeds the pressure within said member.

8. The device of claims 6 or 7 in which said neck portion is provided with a tubular connector and said tubular member is detachably coupled to said connector.

9. The device of claim 8 in which said tubular member is formed in two sections joined together in coaxial relation; said one-way valve means comprising a flap valve formed of resilient material having a peripheral ring portion disposed between said sections to provide a sealing gasket therebetween; said flap valve also including a central flap portion integral with said ring portion; and a valve seat within said tubular member normally engaged by said flap portion to prevent reverse flow of urine therethrough.

10. A female urinary incontinence device comprising a periurethral cup formed of soft elastomeric material having an upwardly-opening urine-receiving cavity and a continuous rim extending about the opening of such cavity; said cup also including front and rear portions and an integral downwardly-extending neck portion of reduced width having a passage communicating with said cavity, said neck portion being provided with connecting means for connection to a drainage tube; first resilient adhesive pad means externally affixed to said neck portion; said first pad means comprising at least one strip of pressure-sensitive adhesive material having a pair of side sections providing enlarged laterally-facing adhesive surfaces extending longitudinally along opposite sides of said neck portion for adhesively engaging the inwardly-facing side surfaces of the labia minora of a patient; and second resilient adhesive pad means of annular shape affixed to said rim along the full extent thereof for sealing engagement with a patient about the urethral orifice.

11. The device of claim 10 in which said side sections of said first pad means extend forwardly beyond said neck portion.

12. The device of claims 10 or 11 in which said first pad means has a dimension measured longitudinally of said neck portion within the range of about 5 to 20 millimeters.

13. The device of claim 12 in which said neck portion with said first adhesive pad means thereon have a maximum outside lateral dimension within the range of 10 to 16 millimeters.

14. The device of claims 10 or 11 in which said first pad means comprises a single strip of adhesive material wrapped about the rear side of said neck portion with the end portions of said strip joined together to form a double-thickness flap projecting forwardly from said neck portion directly beneath said cup.

15. The device of claim 10 in which said neck portion is connected to and communicates with a tubular member having one-way valve means therein for preventing a reverse flow of urine into said neck portion and said cup; and vent means between said valve means and said neck portion for permitting the entry of ambient air into said neck portion when ambient pressure exceeds the pressure within said tubular member.

16. The device of claim 15 in which said vent means comprises a lateral passage in said tubular member having a valve seat therein; a resilient, imperforate valve disc disposed within said passage having its periphery normally engaging said seat to prevent the escape of urine from said tubular member but being capable of flexing away from said seat to permit the entry of air when ambient pressure exceeds the pressure within said member.

17. The device of claims 15 or 16 in which said neck portion is provided with a tubular connector and said tubular member is detachably coupled to said connector.

18. The device of claim 17 in which said tubular member is formed in two sections joined together in coaxial relation; said one-way valve means comprising a flap valve formed of resilient material having a peripheral ring portion disposed between said sections to provide a sealing gasket therebetween; said flap valve also including a central flap portion integral with said ring portion; and a valve seat within said tubular member normally engaged by said flap portion to prevent reverse flow of urine therethrough.

19. A female urinary incontinence device comprising a periurethral cup formed of soft elastomeric material having integral front and rear portions; said rear portion projecting upwardly to provide a vaginally-insertable urine-deflecting protuberance; said front and rear portions together defining an upwardly-opening-urine-receiving cavity having a continuous rim that faces generally upwardly along said front portion and both upwardly and forwardly along said rear protuberant portion; said cup also including an integral downwardly-extending neck portion of reduced width having a passage communicating with said cavity; first resilient adhesive pad means externally affixed to said neck portion; said first adhesive pad means comprising at least one strip of pressure-sensitive adhesive material having a pair of side sections extending longitudinally along opposite sides of said neck portion and having vertically enlarged laterally-facing surfaces for adhesively engaging the inwardly-facing side surfaces of the labia minora of a patient; and second resilient adhesive means of annular shape affixed to said rim along the full extent thereof; said second adhesive pad means having a front section extending along the rim of said cup's front portion for engaging the periurethral floor of a patient and having a rear section extending along the rim of the cup's rear protuberant portion for engaging the vaginal introitus.

20. The device of claim 19 in which said side sections of said first adhesive pad means extend forwardly beyond said neck portion beneath said front portion of said cup.

21. The device of claim 19 or 20 in which said first adhesive pad means provides lateral surfaces with a vertical dimension within the range of about 5 to 20 millimeters.

22. The device of claim 21 in which said neck portion and said first adhesive pad means have outside lateral dimensions within the range of about 10 to 16 millimeters.

23. The device of claim 21 in which said rim curves smoothly and gradually at the merger between said front and rear portions of said cup.

24. The device of claims 19 or 20 in which said first pad comprises a strip of adhesive material wrapped about the rear side of said neck portion with the end portions of said strip joined together to form a double-thickness flap projecting forwardly from said neck portion beneath said front portion of said cup.

25. The device of claim 19 in which said neck portion is connected to and communicates with a tubular member having one-way valve means therein for preventing a reverse flow of urine into said neck portion and said cup; and vent means between said valve means and said neck portion for permitting the entry of ambient air into said neck portion when ambient pressure exceeds the pressure within said tubular member.

26. The device of claim 25 in which said vent means comprises a lateral passage in said tubular member having a valve seat therein; a resilient, imperforate valve disc disposed within said passage having its periphery normally engaging said seat to prevent the escape of urine from said tubular member but being capable of flexing away from said seat to permit the entry of air when ambient pressure exceeds the pressure within said member.

* * * * *